United States Patent [19]

Rafelson

[11] Patent Number: 4,662,871

[45] Date of Patent: May 5, 1987

[54] DISPOSABLE SUCTION CATHETER AND SYSTEM FOR PROVIDING MULTIPLE SUCTIONING CAPABILITIES DURING MEDICAL PROCEDURES OR THE LIKE

[76] Inventor: Stephen Rafelson, 20 Stratford La., Mount Laurel, N.J. 08054

[21] Appl. No.: 651,829

[22] Filed: Sep. 18, 1984

[51] Int. Cl.⁴ .............................................. A61M 1/00
[52] U.S. Cl. .................. 604/119; 604/250; 604/902; 128/4
[58] Field of Search ............... 604/902, 118-120, 604/30-36, 27, 28, 19, 48, 73, 49-54, 65, 66, 93, 128, 129, 131, 175, 190, 319, 322; 433/50, 53, 91, 94-96, 99, 100, 108; 128/4, 5-8

[56] References Cited

U.S. PATENT DOCUMENTS

| | | | |
|---|---|---|---|
| 1,152,818 | 9/1915 | Kells | 604/902 |
| 2,638,670 | 5/1953 | Wyne | 433/95 |
| 3,027,644 | 4/1962 | Piscitelli | 433/100 |
| 3,169,528 | 2/1965 | Knox, III, et al. | 604/281 |
| 3,191,600 | 6/1965 | Everett | 604/120 |
| 3,256,885 | 6/1966 | Higgins et al. | 604/281 |
| 3,395,705 | 8/1968 | Hamilton | 604/119 |
| 4,068,664 | 1/1978 | Sharp et al. | 604/268 |
| 4,118,866 | 10/1978 | Ross et al. | 433/100 |
| 4,270,525 | 6/1981 | Furihata | 604/119 |
| 4,321,921 | 3/1982 | Laszczower | 604/35 |
| 4,400,168 | 8/1983 | Buechel et al. | 604/48 |
| 4,414,974 | 11/1983 | Dotson et al. | 128/305 |
| 4,519,385 | 5/1985 | Atkinson et al. | 604/902 |

OTHER PUBLICATIONS

Ureteral Catheters, American Cystoscope Makers Inc., catalogue (AU336), (1960).

Primary Examiner—Dalton L. Truluck
Assistant Examiner—Mario Costantino
Attorney, Agent, or Firm—Mason, Fenwick & Lawrence

[57] ABSTRACT

A multiple suctioning system, particularly for use in endoscopic procedures or the like, which is provided with a suction source, a Y-shaped connector which is provided with a rotatable stopcock and a plug-like stopper, at least three segments of pliable tubing, and a suction catheter which comprises an elongated handle, a deformable tip, means for preventing the tip from plugging, means for anchoring the catheter in a convenient location, bright-colored vinyl plastic tubing to connect the catheter to a suction source, means for attaching the tubing to the catheter, and means for controlling the flow of suction forces through the catheter.

32 Claims, 21 Drawing Figures

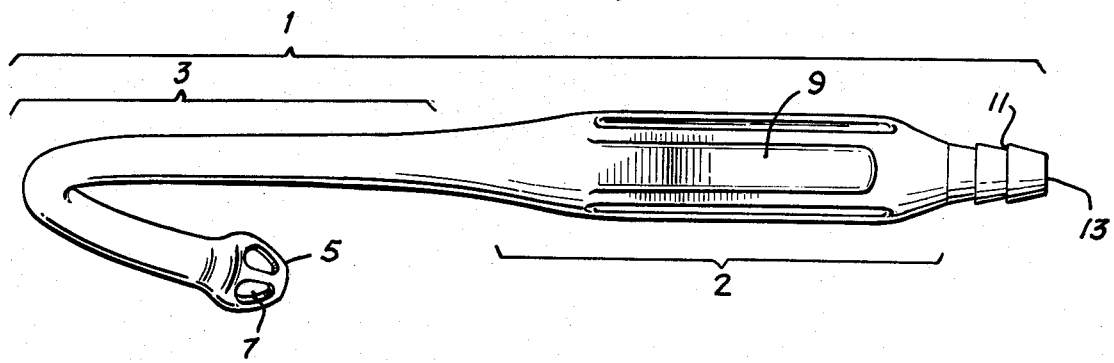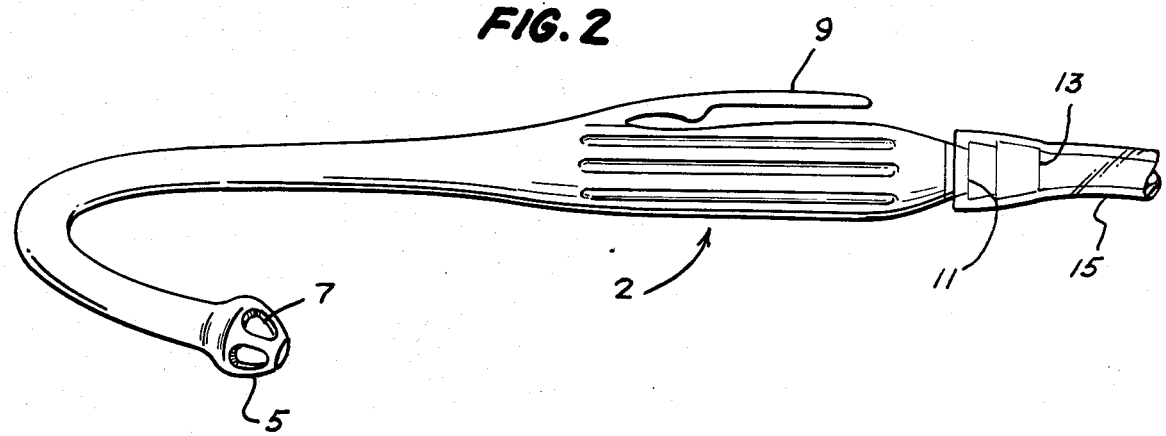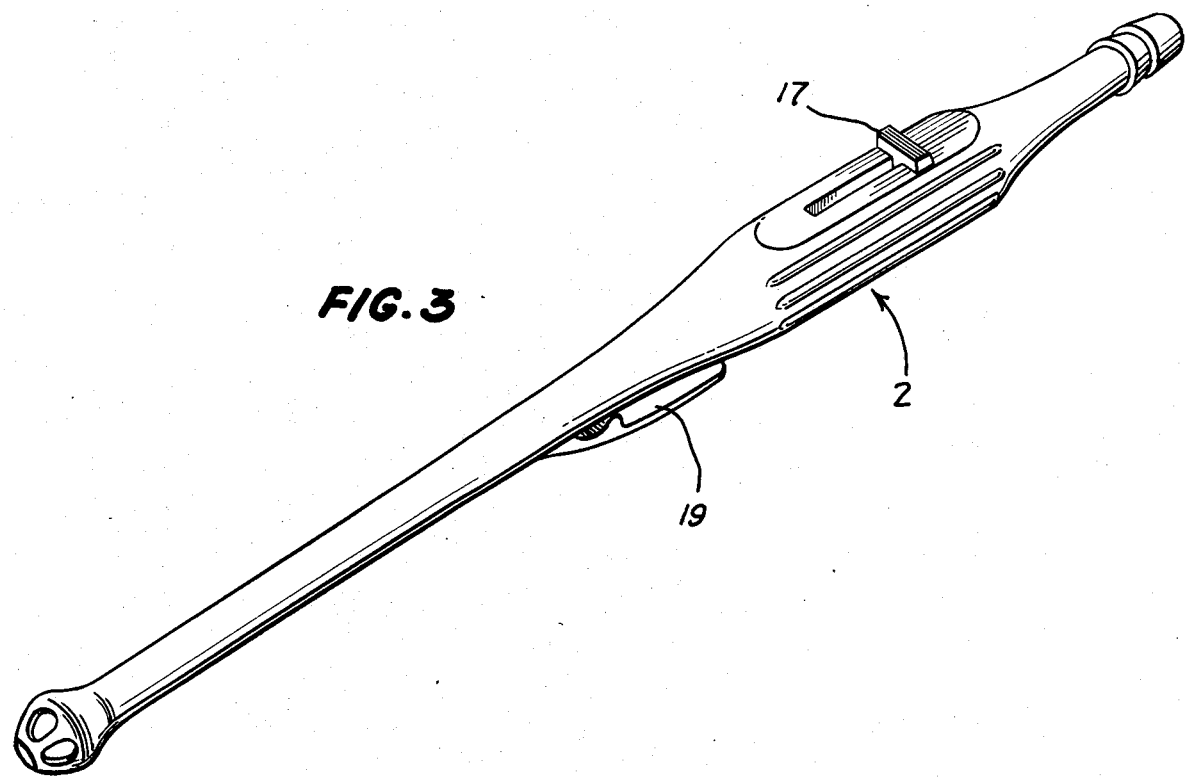

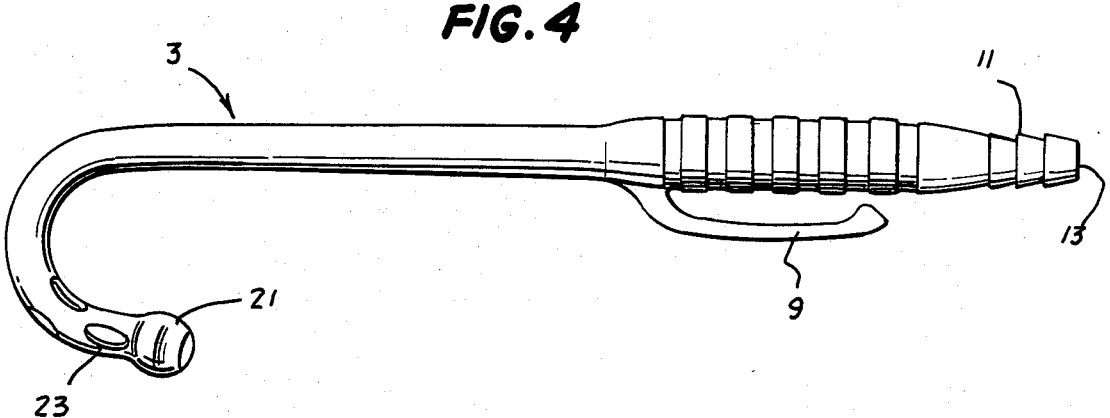
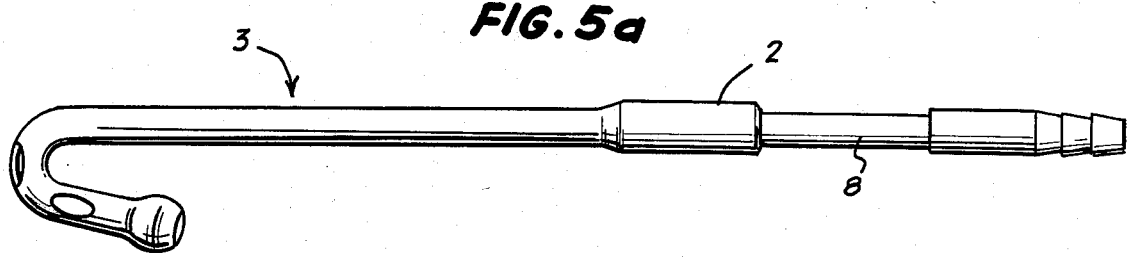
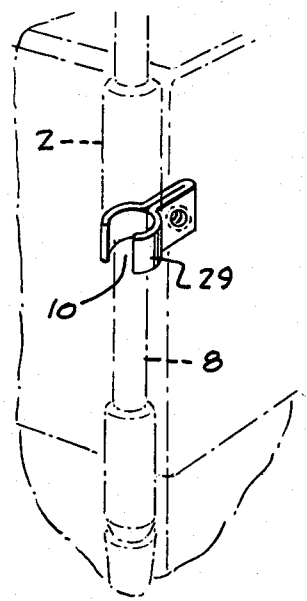
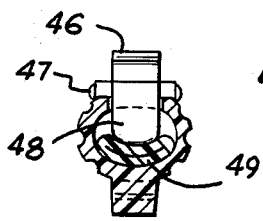
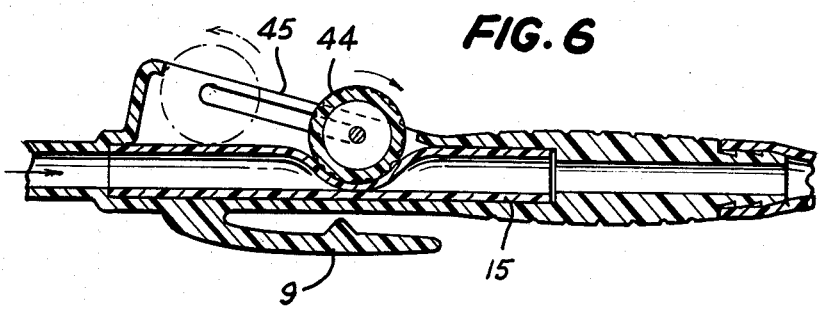
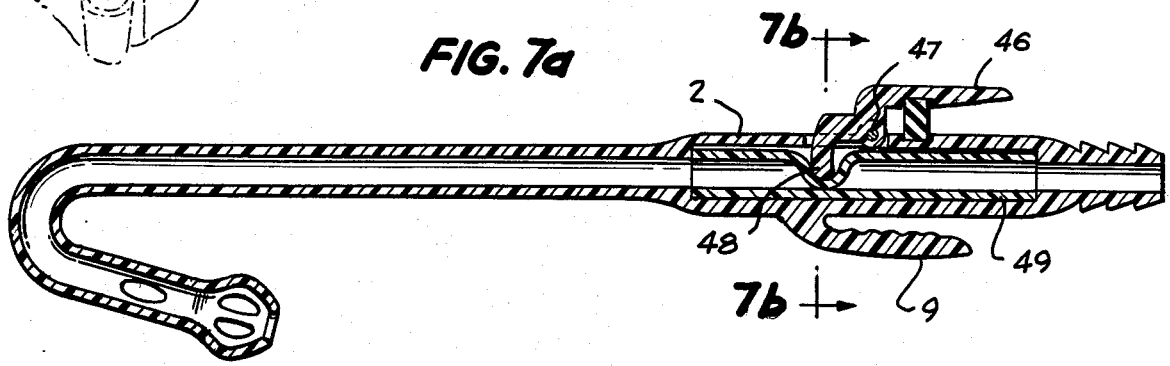

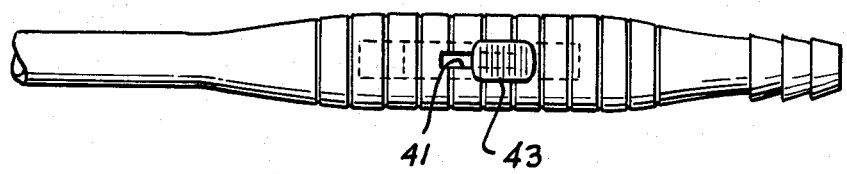
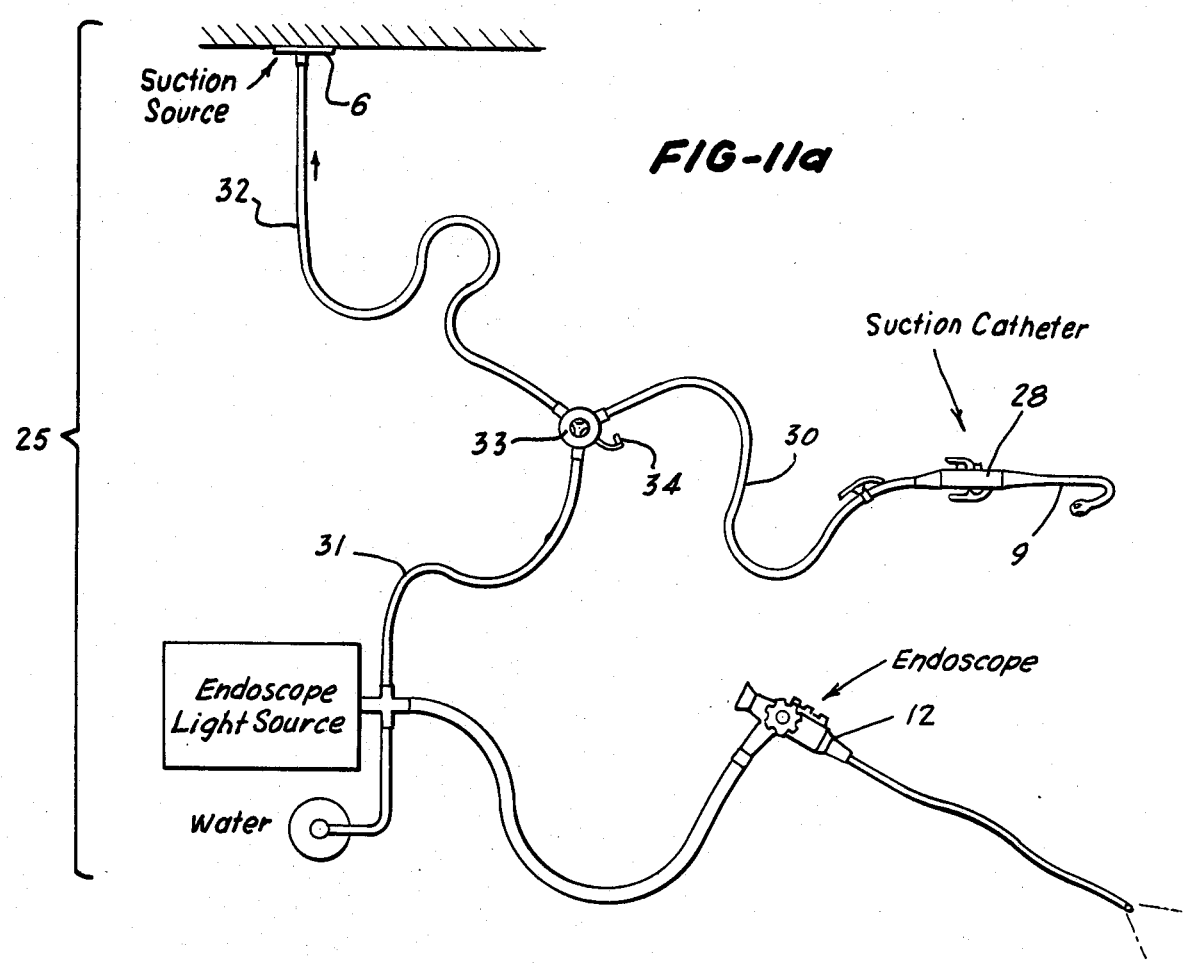
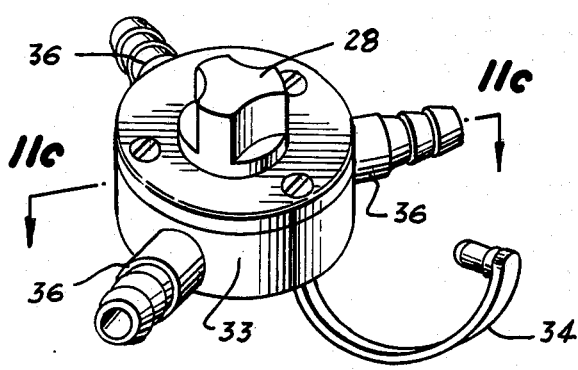
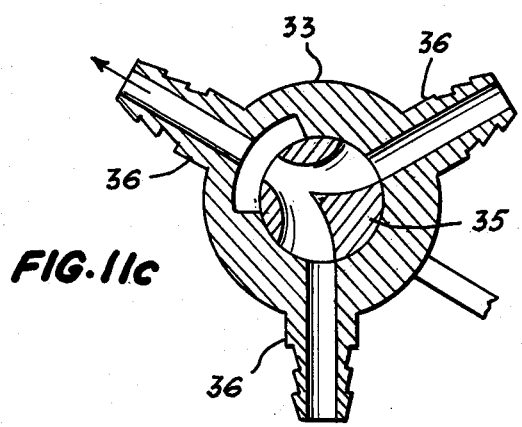

DISPOSABLE SUCTION CATHETER AND SYSTEM FOR PROVIDING MULTIPLE SUCTIONING CAPABILITIES DURING MEDICAL PROCEDURES OR THE LIKE

BACKGROUND OF THE INVENTION

The present invention relates to disposable suction catheters, and more particularly to disposable suction catheters for use during many medical or dental procedures, such as endoscopy and bronchoscopy. The present invention also relates to a system for providing multiple suctioning capabilities from a single suction source during medical procedures or the like.

Ordinarily, upper gastrointestinal endoscopy is carried out with the patient lightly sedated. The patient is usually in the left lateral decubitus position with the head resting on a form of support, usually a pillow. During the course of the endoscopic procedure, the oral cavity must be kept free of secretions while the patient's cough and gag reflexes are depressed in order to prevent aspiration with resultant hypoxia and its complications. Therefore, it is often necessary for the nurse or physician to provide suctioning to both the endoscopic instrument and the patient's oral cavity. Usually, two separate suctioning devices or outlets are required to accomplish these tasks. This is quite cumbersome in those circumstances where one suction source would be sufficient, such as with endoscopically conducted X-ray examinations of the bile and pancreatic ducts, or slim scope endoscopy of the unobstructed, "well" patient. Further, the necessity for two suction units in the room at once causes delay in transporting suction equipment, causes crowding in the examination room, and generates excessive noise from having two separate suction units in the room at one time. These inconveniences can become critical under emergency conditions, particularly in crowded emergency rooms.

Presently, there are no devices which enable the physician to have easy access to the oropharyngeal suction catheter during the course of an endoscopic procedure. The catheter is often inconveniently placed beyond the reach of the nurse and/or doctor or just forgotten. It is not an uncommon practice for nurses to place suction catheters in hard to reach locations, such as in their pockets, on IV pole receptacles, or under the patient's pillow. This practice causes considerable delay in applying suction to the oral cavity while the nurse or doctor turns to find the equipment and transport it to the endoscopic table. In fact, suction catheters are frequently dropped on the floor and reused by medical personnel due to the poor design of the catheters presently in use. Such lapses in technique can predispose susceptible individuals to pneumonia or exacerbations of their underlying disease states, such as coronary artery disease or chronic bronchitis. Further, patients who require, but do not receive, suctioning of the oropharynx, are much harder to sedate and may inappropriately receive more sedation, instead of the needed suctioning which can relieve them of the sensation of drowning in their own secretions. These problems are compounded by the fact that most suction catheters presently in use are connected to the suction source by transparent vinyl tubing which is difficult to see when lying against white hospital bedding in a dark room. Also, suction instruments currently in use contribute an irritating and distracting "hissing" noise to the working environment. This undesirable feature is eliminated by the catheter of the present invention by blocking air flow when the catheter is in the resting "off" mode At the present time, routine endoscopic examinations of the bile and pancreatic ducts require simultaneous suctioning to two different areas: the patient's oral cavity and the endoscopic instrument itself. Although the endoscope is equipped with suctioning capabilities and controls, suctioning is not continuously needed during the course of a routine endoscopic procedure. It is clear that some of the suction force could be diverted by Y-tubing to an alternately closed/open system catheter devoted to oral cavity hygiene. Consequently, it is quite inconvenient and/or impractical in many settings, even in specialized areas of a hospital or GI units, to obtain dual suction capabilities, one of which is specially earmarked for the patient's oropharynx.

To meet this need, the multiple suctioning system of the present invention is provided with a disposable detachable limb of Y-tubing which leads to the patient's oropharynx and a reusable limb of Y-tubing which connects with the umbilical cord or suction port of an endoscope or the like. The oral cavity suction catheter performs as a standard suction catheter, but remains in a non-suctioning mode when in the resting state. A spring-action catheter, clip-trigger or the like is provided on the surface of the catheter handle to allow the suctioning to be intermittently applied only when needed.

By remaining in the closed position much of the time, the catheter of the present invention allows suctioning to be by passed when not needed, thus producing continuous suction for the endoscope, where suctioning is most often needed. When it is necessary for the physician or operator to provide oral suctioning for several seconds, this brief lapse or decrease in suctioning to the endoscope would not be detrimental or inconvenient.

SUMMARY OF THE INVENTION

The present invention overcomes the aforementioned disadvantages of the prior art by providing a suction catheter which includes a means for anchoring the catheter in a convenient location when the catheter is not immediately needed during the course of an endoscopic procedure. Further, the catheter of the present invention is provided with a deformable tip which can be utilized in a straight or a curved position. The catheter and/or flexible tubing which connects the catheter of the present invention to the suction source is manufactured in a bright, easily-visible color which contrasts with the sheets and bedding ordinarily used by hospitals. The distal end of the catheter tip of the present invention is designed to retard plugging by mucous membranes of the mouth so that continuous suctioning is available. In one embodiment, the catheter of the present invention is provided with a simple trigger-controlled occluder which allows suction forces to bypass the endoscope temporarily and briefly service the oral cavity when needed, both an endoscope or the like and the catheter are connected to one suction source by means of Y-shaped tubing.

In order to provide more versatility during procedures which reguire suctioning, the present invention provides for disposable tubing with a Y-shape configuration wherein one limb of the Y, that which provides suction to the oropharynx, can be removed and replaced with another limb. This provides convenient dual suction sources for both the patient and the endoscopic instrument. The removability at the junction of both limbs allows for smaller amounts of wasted material than when the entire apparatus is disposed of after each individual patient use. The limb leading from the suction source to the patient's oropharynx can be of a smaller caliber or bore than the limb leading from the suction source to the endoscope itself. When the catheter is provided with a trigger control, suctioning can continue in the endoscope most of the time. Thus, when the trigger of the catheter connected to the smaller bore tubing is depressed, it interferes less with the suction to the instrument by virtue of its narrower caliber and greater resistance to the flow of air.

The oral suction catheter can be permanently fastened to the Y limb of the narrow bore 'patient' tubing or it can be designed to be detachable so that different shaped oral suction catheters can be chosen. However, permanent attachment of catheter to tubing is convenient because then the only attachment necessary at the start of endoscopy is the linkup of this limb with the Y connector permanently attached to the semi-permanent large bore limb, which leads to the endoscopic instrument.

It also is possible to operate trigger-controlled catheters independently, such as when it is desirable to eliminate unnecessary noise. The catheter can easily be turned on again by applying pressure to the trigger. Most devices which are presently available commercially are provided with venting ports along the body of the catheter which, if covered by the finger, activate suction at the tip of the device. However, a main shortcoming of these devices is the continuous noise produced by air forced into the vent ports by suction forces when the catheter is not in use.

Thus, it is a primary object of the present invention to provide a suction catheter, particularly for use in endoscopic procedures, which can be anchored in a convenient location in the examination room so that the catheter is readily accessible to the attending medical personnel during the course of the procedure.

Another object of the present invention is to provide a suction catheter which is easily visible in dark examination rooms during the course of a medical procedure.

An additional object of the present invention is to provide a suction catheter which can be adapted to the particular contour of the patient's oral anatomy and anchored in this location if necessary.

Yet another object of the present invention is to provide a suction catheter which can be modified during a procedure to enable deeper pharyngeal suctioning when required.

A still further object of the present invention is to provide a catheter which will transmit the suction forces intermittently during the course of a medical procedure.

Still a further object of the present invention is to provide a suction catheter which is resistant to plugging by the mucous membranes of the oropharyngeal cavity during the suctioning operation.

It is also an object of the present invention to provide a multiple suctioning system having disposable tubing with a Y-shaped configuration so that a suction catheter and a medical instrument can be attached simultaneously to one suction source.

Other objects and features of the present invention will become apparent to those skilled in the art as the disclosure is made in the following description of the preferred embodiments of the invention as illustrated in the accompanying sheets of drawings.

BRIEF DESCRIPTION OF THE DRAWINGS

FIG. 1 is a top plan view of the catheter of the present invention.

FIG. 2 is a lateral side view of the catheter of the present invention showing the location of the clip.

FIG. 3 is a perspective view of another embodiment of the catheter of the present invention showing the catheter in a straight position and showing the addition of a trigger mechanism with a sliding occluder.

FIG. 4 is a lateral side view of another embodiment of the device shown in FIG. 2 wherein the clip is located in an alternate position.

FIG. 5(a) illustrates a lateral side view of another embodiment of a tip and handle of the catheter.

FIG. 5(b) is a perspective view of a ring which cooperates with the handle shown in FIG. 5(a).

FIG. 6 is a lateral cross-sectional view illustrating a regulator wheel as a trigger mechanism in the catheter of the present invention.

FIG. 7(a) is a lateral cross-sectional view of a lever-fulcrum type trigger mechanism in the catheter of the present invention.

FIG. 7(b) is a cross-sectional view of the catheter shown in FIG. 7(a).

FIG. 10(b) is a top view of the catheter shown in FIG. 10(a).

FIG. 11(a) is a side view of the multiple suctioning system of the present invention showing a suction catheter and an endoscope connected to a single suction source with a Y-shaped connector.

FIG. 11(b) is an enlarged view of the Y-shaped connector shown in FIG. 11(a).

DETAILED DESCRIPTION OF THE PREFERRED EMBODIMENTS

Figure 6A:
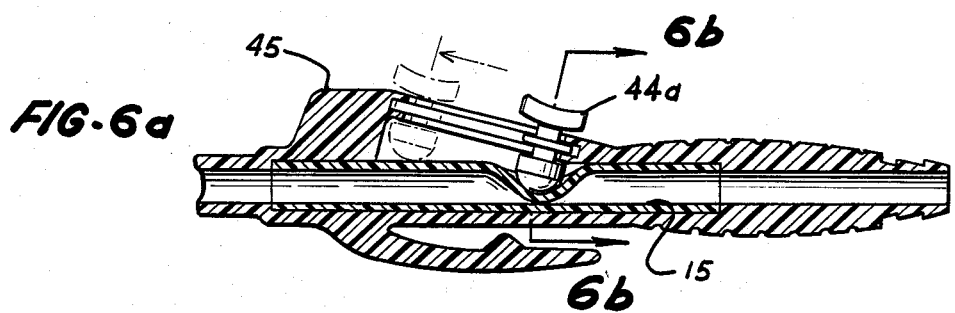
FIG. 6(a) is a lateral cross-sectional view of sliding occluder which provides external compression on vinyl tubing.

Referring now to the drawings, there is shown in FIG. 1, a disposable endoscopic suction catheter 1 according to the present invention which is provided with an elongated, hollow section for use as a handle 2. Preferably, handle 2 is of a size which fits comfortably in the palm of the hand. Tip 3 is integrally molded or attached to one end of handle 2. The oropharyngeal secretions are drawn through tip 3 by the suction forces originating from a mechanical suction source (not shown). The opposite end of handle 2 tapers slightly to form connector end 13, to which is attached flexible tubing 15. Raised ridges 11 or the like are provided around the circumference of connector end 13 to prevent tubing 15 from detaching from the catheter during use.

Handle 2 is provided with a means for anchoring catheter 1 in a convenient location at the site of the endoscopic procedure. For instance, as shown in FIG. 1, handle 2 is provided with clip 9, which is similar to a pen clip, and which can be attached to the pillow slip, the bedding, or one of the pieces of equipment normally utilized during medical procedures. Clip 9 may be located on the main body of handle 2, as shown in FIGS. 1 and 2, or on the body of tip 3, as shown in FIG. 3.

Figure 8A:
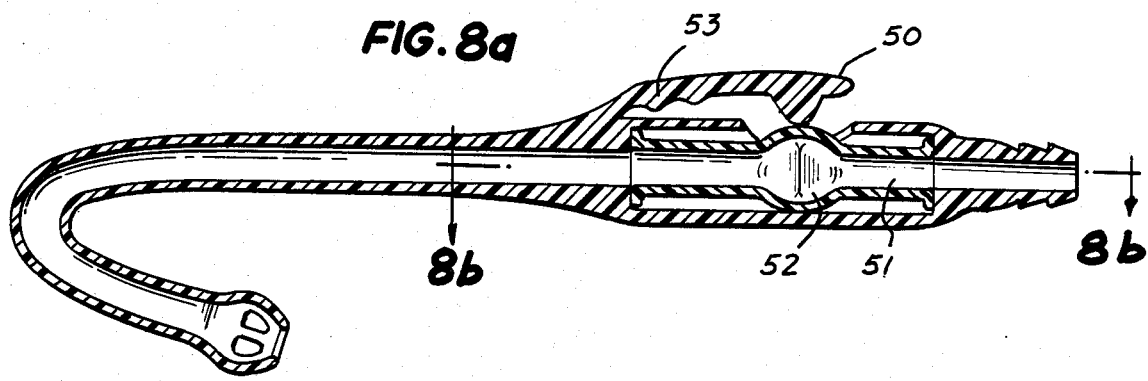
FIG. 8 is a lateral cross-sectional view of a combination clip and trigger mechanism.
Figure 8B:
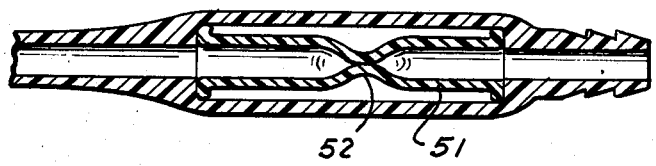

Several other anchoring means also are suitable for use in the catheter of the present invention. In FIG. 8, there is shown a type of clip 50 having a serated underside 53 which is attached to the body 4 of tip 3.

Alternately, handle 2 can be manufactured with an elongated indentation 8 around the circumference of handle 2, as seen in FIG. 5(a). Indentation 8 cooperates with a separate ring 29, shown in FIG. 5(b). Ring 29 is provided with slit 10 through which handle 2 is forced so that catheter 1 is retained by ring 29 when not in use. The diameter of handle 2 at indentation 8 is egual to the width of slit 10, as indicated by reference a, so that handle 2 slips easily through slit 10 in ring 29. Thus, handle 2 can be removed quickly by forcing handle 2 out through slit 10 when catheter 1 is needed. Ring 29 can be located on a vital sign module or any other piece of equipment ordinarily found in an examination room.

Tip 3 is provided with a body portion 4 and a distal end 5. Preferably, tip 3 is constructed from a deformable or pliable material to allow the tip to be used in a curved configuration, as shown in FIGS. 1 and 2, or in a straight configuration, as shown in FIG. 3. Tip 3 can be either permanently or removably attached to handle 2. Although standard male/female connectors or luerlock type connectors may be used, it is preferable that tip 3 be permanently attached to handle 2. Handle 2 and tip 3 preferably are manufactured from a bright-colored material which makes the disposability of catheter 1 commercially feasible, such as plastic, vinyl or a similar synthetic or rubber.

Distal end 5 of tip 3 is provided with multiple radially directed ports 7 to prevent the mucous membranes of the oral cavity from plugging the tip during use. Ports 7 may also be staggered around tip 3 a few centimeters from distal end 5. Distal end 5 can have a bulbous shape, as in FIG. 1, or have a straight, smooth shape, as in FIG. 4. In the embodiment shown in FIG. 4, distal end 21 of tip 3 is provided with oval shaped orifices.

In one preferred embodiment of the present invention, handle 2 is provided with a means for intermittently allowing the suction forces from a mechanical suction device to service catheter 1. When Y-shaped tubing is connected to a single strong suction source to provide suction to both the catheter and the endoscope, a trigger mechanism 17, shown generally in FIG. 3, may be provided to allow suction forces to temporarily bypass the endoscope and briefly service the oral cavity. Alternately, when one standard single source of suctioning is used in the oral cavity and a second source independently handles endoscopic suction capabilities, the suctioning can be made quieter by using the trigger operated catheters of the present invention.

An alternate trigger mechanism is shown in FIG. 7, wherein lever 46 cooperates with fulcrum 47 and occluder 48 to continuously pinch inner flexible tubing 49 when occluder 48 is in a resting state, thereby blocking the air flow passageway. However, when lever 46 is pressed against fulcrum 47, occluder 48 is released and the suction forces can pass through flexible tubing 49 to clear the oral cavity of secretions.

Figure 6C:
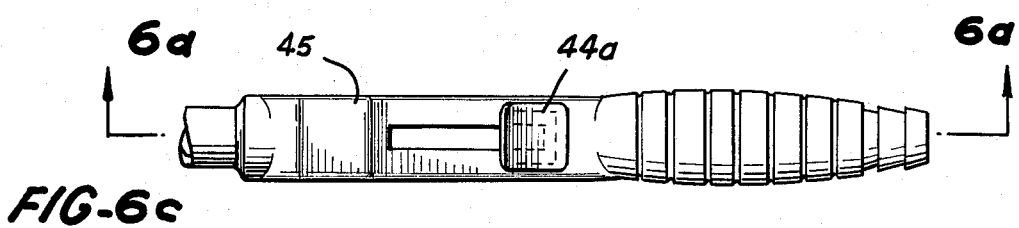
FIG. 6(c) is a top view of the catheter shown in FIG. 6(a).
Figure 6B:
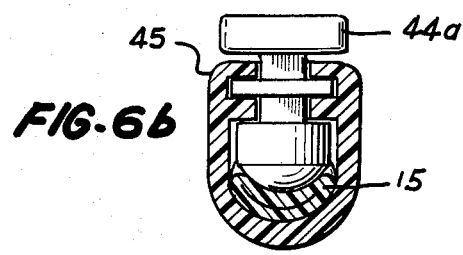
FIG. 6(b) is a frontal cross-sectional view of the catheter shown in FIG. 6(a).

Another embodiment of a trigger mechanism is shown in FIGS. 6 and 6a whereby regulator wheel 44 or occluder 44a cooperates with raised portion 45 of handle 2 so that when regulator wheel 44 or occluder 44a is rolled or moved toward connector end 13 of handle 2, flexible tubing 15 is pinched between regulator wheel 44 or occluder 44a and the ridged plastic wall of handle 2. Raised portion 45 is manufactured as an integral part of handle 2. Regulator wheel 44 or rigid occluder 44a are simply rolled or moved toward tip 3 to allow flexible tubing 15 to spring back to its original shape so that the suction forces can pass through tubing 15.

Figure 9A:
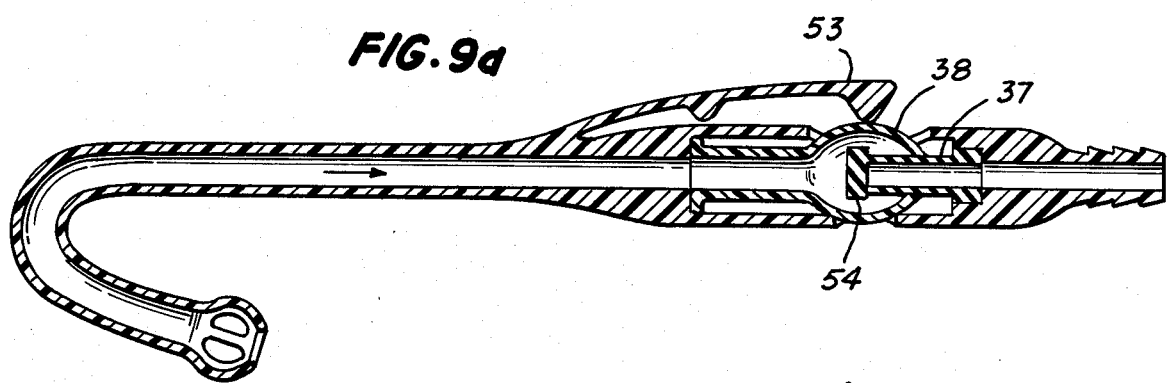
FIG. 9 is a lateral cross-sectional view of a catheter which is provided with a one-way valve as a trigger mechanism.
Figure 9B:
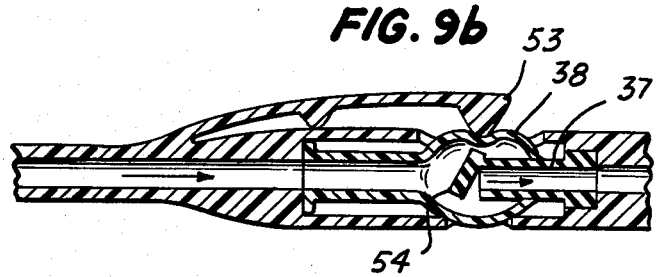

FIG. 9 shows a trigger mechanism which utilizes a one way valve 54 which is operated by clip 53. When clip 53 is pressed against outer plastic bubble 38 in vinyl tubing 37, inner collapsable closed end vinyl tubing 37 is deformed, exposing suction forces at the rear of the bubble and within the tubing to the previously closed off proximal vinyl tubing located closest to the patients' oropharynx, as shown in FIG. 9.

In FIG. 8 there is shown a trigger mechanism whereby handle 2 is provided with a piece of pliable vinyl tubing 51, the sides of which remain tightly pressed together at section 52 of tubing 51 when catheter 1 is in the closed position. When clip 50 is pressed against section 52, the sides of tubing 51 are separated and the suction forces can pass freely through vinyl tubing 51 in catheter 1.

Although tubing 15 ordinarily is made of flexible vinyl plastic, any suitable material can be used. It is preferable that flexible tubing 15 and/or catheter 1 be manufactured in a bright color which provides a sharp contrast to the white backgrounds normally found in hospitals. This allows for easy recognition in the dark, poorly lit environments often necessary for many medical procedures, particularly the endoscopic procedure. Flexible tubing 15 may be permanently or removably attached to connector end 13 of catheter 1.

Figure 10A:
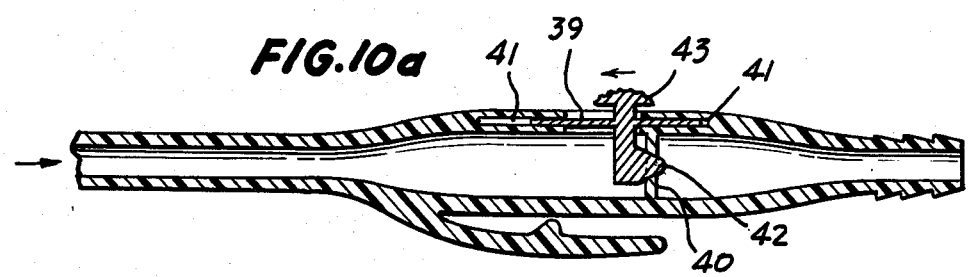
FIG. 10(a) is a lateral cross-sectional view of a catheter which is provided with a sliding occluder mechanism.

As seen in FIG. 10(a), another type of trigger mechanism, such as sliding internal occluder 42, can be provided on catheter 1. Sliding internal occluder 42 cooperates with surface projection 43 which extends to the upper surface of handle 2 through slit 41. Both internal occluder 42 and surface projection 43 are attached to flat plate 39 in slit 41. When surface projection 43 on handle 2 is moved toward connector end 13, internal occluder 42 is pressed against circumferential projections 40 within handle cross-blocking the air flow. When internal occluder 42 is in a resting state, the air flow is blocked. When surface projection 43 is moved toward distal end 5 of catheter 1, internal occluder 42 is forced away from projections 40 allowing air to pass through.

FIG. 11(a) illustrates the multiple suctioning system 25 of the present invention wherein a trigger-controlled catheter and an endoscope are used in conjunction with a Y-shaped tubing arrangement to provide multiple suctioning capabilities from a single suction source. In multiple suctioning system 25, tubing segment 32 connects suction source 6 with Y-shaped connector 33. Y-shaped connector 33 is provided with multiple arms 36, all of which are connectable to segments of soft plastic or vinyl tubing. A rotatable stopcock 35 is provided in the center of connector 33 to direct the suction forces through either one or two segments of vinyl tubing. Rotatable stopcock 35 can be provided with knob 28 or the like to facilitate rotation. Y-shaped connector 33 may also be provided with a floppy, plastic plug-type stopper 34 or the like to close off one arm of Y-shaped connector 33 when dual suctioning capabilities are not necessary, such as during a colonoscopy or during a flexible sigmoidoscopy.

Tubing segment 32 can be made in varying lengths, but is preferably between 36 to 48 inches in length. Tubing segment 32 can be made of soft plastic or vinyl tubing which is inexpensive and disposable. A second tubing segment 30 is attached to a second arm 36 of Y-shaped connector 33 to connect the suction source with trigger-controlled suction catheter 9. Any of the above-described trigger-controlled suction catheters are suitable for use in multiple suctioning system 25 of the present invention. A third tubing segment 31 is attached to one of the arms 36 of the Y-shaped connector 33 to connect the suction source 6 with endoscope 12 or any other instrument reguiring suction capabilities during use. Tubing segment 30 connecting suction catheter 9 with Y-shaped connector 33 can be smaller in diameter or bore than tubing segment 32 so that the suction forces along tubing segments 31 and 32 remain somewhat intact when suction catheter 9 is activated by controlling the integral trigger 28.

Having described the invention, many modifications thereto will become apparent to those skilled in the art to which it pertains without deviation from the spirit of the invention as defined by this scope of the appended claims.

What is claimed is:

1. A suction catheter for use in endoscopic procedures in combination with an endoscope, said suction catheter and said endoscope being connected to a common suction source, said suction catheter comprising:
   an elongated handle;
   a tip having a body portion, a distal end and port means through which secretions are drawn, the body portion of said tip being attached to said handle;
   means for preventing said port means from plugging;
   passage means defined by said tip and said elongated handle for flow of suction forces from said port means to said suction source;
   means for anchoring said catheter in a convenient location near the site of said endoscopic procedures so that said catheter is easily accessible; and
   adjusting means defined by said elongated handle for controlling said suction forces flowing through said catheter to said suction source, said adjusting means being closed to cause said suction forces to flow through said endoscope to said suction source while said suction catheter remains in a non-suctioning mode and said adjusting means being open to allow said suction forces to flow through suction catheter and said endoscope.

2. A suction catheter according to claim 1 wherein said means for preventing the port means from plugging are multiple ports located in the distal end of said tip.

3. A suction catheter according to claim 1 wherein said elongated handle and said tip are formed from bright-colored, flexible vinyl plastic for visibility in dim light.

4. A suction catheter according to claim 1 wherein said means for anchoring said catheter is a clip which is attached to the handle of said catheter.

5. A suction catheter according to claim 4 wherein said clip is attached to the body of said tip.

6. A suction catheter according to claim 1 wherein said means for anchoring said catheter is an indentation in said handle which cooperates with a ring located on a piece of equipment at the site of said endoscopic procedure.

7. A suction catheter according to claim 1 wherein said adjusting means is a regulator wheel which cooperates with a raised portion in said handle to prevent the suction forces from flowing through said catheter.

8. A suction catheter according to claim 7 wherein a sliding occluder cooperates with said raised portion in said handle to prevent the suction forces from flowing through said catheter.

9. A suction catheter according to claim 1 wherein said adjusting means is a fulcrum type device which cooperates with a clip on said handle to prevent said suction forces from passing through said catheter.

10. A suction catheter according to claim 1 wherein said adjusting means is a piece of pliable tubing positioned in the center of said handle which cooperates with a clip to prevent said suction forces from passing through said catheter, said tubing having a middle section in which the sides are tightly pressed together when said suction forces are prevented from flowing through said catheter.

11. A suction catheter according to claim 1 wherein said adjusting means is a one way valve which cooperates with a clip to allow said suction forces to pass through said catheter when said clip is pressed against said one way valve.

12. A suction catheter according to claim 1 wherein said adjusting means is an occluder slidably mounted within said handle, said occluder cooperating with a diaphragm placed within said handle which is closed by said occluder when said occluder is pressed against said diaphragm.

13. A suction catheter according to claim 2 wherein said adjusting means is a regulator wheel which cooperates with a raised portion in said handle to prevent the suction forces from flowing through said catheter.

14. A suction according to claim 13 wherein a sliding occluder cooperates with raised portion in said handle to prevent the suction forces from flowing through said catheter.

15. A suction catheter according to claim 2 wherein said adjusting means is a fulcrum-type device which cooperates with a clip on said handle to prevent said suction forces from passing through said catheter.

16. A suction catheter according to claim 2 wherein said adjusting means is a piece of pliable tubing positioned in the center of said handle which cooperates with a clip to prevent said suction forces from passing through said catheter, said tubing having a middle section in which the sides are tightly pressed together when said suction forces are prevented from flowing through said catheter.

17. A suction catheter according to claim 2 wherein said adjusting means is a one way valve which cooperates with a clip to allow said suction forces to pass through said catheter when said clip is pressed against said one way valve.

18. A suction catheter according to claim 2 wherein said adjusting means is an occluder slideably mounted within said handle, said occluder cooperating with a diaphragm placed within said handle which is closed by said occluder when said occluder is pressed against said diaphragm.

19. A suction catheter according to claim 3 wherin said adjusting means is a regulator wheel which cooperates with a raised portion in said handle to prevent the suction forces from flowing through said catheter.

20. A suction catheter according to claim 19 wherein a sliding occluder cooperates with said raised portion in said handle to prevent the suction forces from flowing through said catheter.

21. A suction catheter according to claim 3 wherein said adjusting means is a fulcrum-type device which cooperates with a clip on said handle to prevent said suction forces from passing through said catheter.

22. A suction catheter according to claim 3 wherein said adjusting means is a piece of pliable tubing positioned in the center of said handle which cooperates with a clip to prevent said suction forces from passing through said catheter, said tubing having a middle section in which the sides are tightly pressed together when said suction forces are prevented from flowing through said catheter.

23. A suction catheter according to claim 3 wherein said adjusting means is a one way valve which cooperates with a clip to allow said suction forces to pass through said catheter when said clip is pressed against said one way valve.

24. A suction catheter according to claim 3 wherein said adjusting means is an occluder slideably mounted within said hanle, said occluder cooperating with a diaphragm placed within said handle which is closed by said occluder when said occluder is pressed against said diaphragm.

25. The suction catheter according to claim 1
wherein said elongated handle terminates in connection means for connecting a length of flexible tubing to said elongated handle,
said body portion is of a constant cross sectional area and terminates in an end portion, said end portion including a bulbous portion having a diameter greater than the diameter of said body portion and said end portion further including a plurality of ports for preventing said tip from plugging, the diameter of said elongated handle being greater than said body portion, and said end portion being bendable to retain its shape in any desired configuration.

26. A suction catheter according to claim 25 wherein said plurality of ports are located at said bulbous portion.

27. A suction catheter according to claim 25 wherein said adjusting means is a regulator wheel which cooperates with a raised portion in said handle to prevent the suction forces from flowing through said catheter.

28. A suction catheter according to claim 27 wherein a sliding occluder cooperates with said raised portion in said handle to prevent the suction forces from flowing through said catheter.

29. A suction catheter according to claim 25 wherein said adjusting means is a fulcrum-type device which cooperates with a clip on said handle to prevent said suction forces from passing through said catheter.

30. A suction catheter according to claim 25 wherein said adjusting means is a piece of pliable tubing positioned in the center of said handle which cooperates with a clip to prevent said suction forces from passing through said catheter, said tubing having a middle section in which the sides are tightly pressed together when said suction forces are prevented from flowing through said catheter.

31. A suction catheter according to claim 25 wherein said adjusting means is a one way valve which cooperates with a clip to allow said suction forces to pass through said catheter when said clip is pressed against said one way valve.

32. A suction catheter according to claim 25 wherein said adjusting means is an occluder slidably mounted within said handle, said occluder cooperating with a diaphragm placed within said handle which is closed by said occluder when said occluder is pressed against said diaphragm.

* * * * *